US00PP36240P2

(12) United States Plant Patent
Smith

(10) Patent No.: US PP36,240 P2
(45) Date of Patent: Nov. 5, 2024

(54) ***CHRYSANTHEMUM* PLANT NAMED 'CIFZ0110'**

(50) Latin Name: ***Chrysanthemum* x *morifolium***
Varietal Denomination: CIFZ0110

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/445,755

(22) Filed: Jan. 17, 2024

(51) Int. Cl.
*A01H 5/02* (2018.01)
*A01H 6/14* (2018.01)

(52) U.S. Cl.
USPC ..... Plt./289

(58) Field of Classification Search
USPC ..... Plt./289
CPC ..... A01H 5/02; A01H 5/00; A01H 6/1424; A01H 6/14
See application file for complete search history.

(56) References Cited

U.S. PATENT DOCUMENTS

PP25,878 P2 * 9/2015 Smith ..... A01H 5/02 Plt./289

* cited by examiner

*Primary Examiner* — June Hwu
(74) *Attorney, Agent, or Firm* — Dale Skalla

(57) ABSTRACT

A new garden type *Chrysanthemum* plant named 'CIFZ0110' particularly distinguished by its medium size plant with round plant habit, a medium size decorative flower with yellow flower color, and a natural season response in early September.

1 Drawing Sheet

Figure 1:
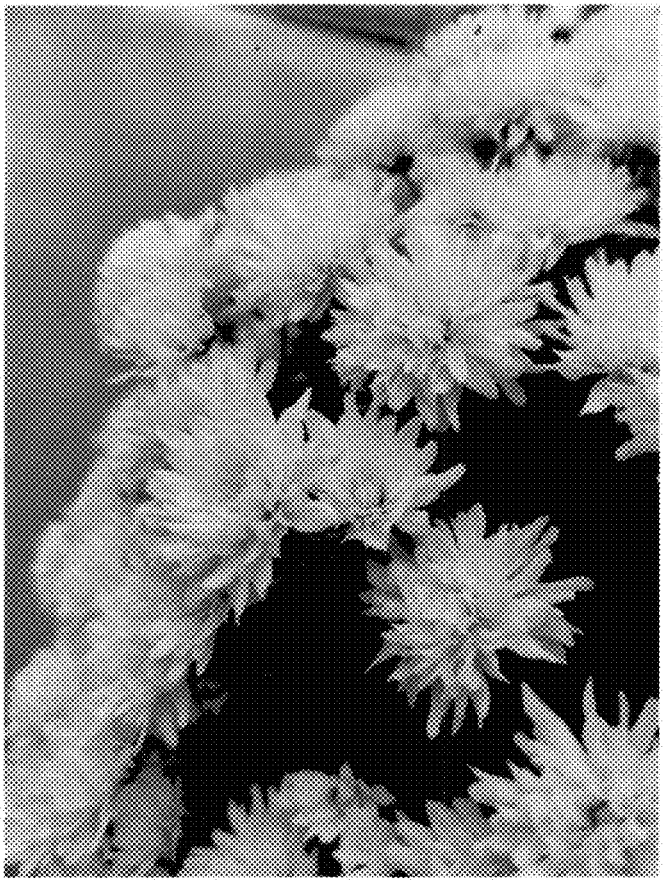

Latin name of the genus and species of the plant claimed: *Chrysanthemum* x *morifolium.*

Varietal denomination: 'CIFZ0110'.

BACKGROUND OF THE NEW PLANT

The present invention comprises a new *Chrysanthemum*, botanically known as *Chrysanthemum* x *morifolium*, and hereinafter referred to by the variety name 'CIFZ0110'.

'CIFZ0110' is a product of a planned breeding program. The new cultivar has a medium size plant with round plant habit, a medium size decorative flower with yellow flower color, and a natural season response in early September.

'CIFZ0110' originated from a cross made in November 2018 in Enkhuizen, The Netherlands. Seeds were sown in June 2019 in Gilroy, California and 'CIFZ0110' was selected from the resulting population on Nov. 25, 2019 in Alva, Florida.

The female parent was 'Venos Yellow', U.S. Plant Pat. No. 29,974

TABLE 1

Characteristics of the female parent, compared to 'CIFZ0110':

| Trait | 'CIFZ0110' | 'Venos Yellow', U.S. Plant Pat. No. 29,974 |
|---|---|---|
| Natural response: | 2 weeks faster | 2 weeks slower |
| Blackcloth response: | 2 weeks faster | 2 weeks slower |
| Flower size: | Similar | Similar |
| Flower color: | Similar | Similar |
| Flower type: | Less disc flowers | More disc flowers |

TABLE 1-continued

Characteristics of the female parent, compared to 'CIFZ0110':

| Trait | 'CIFZ0110' | 'Venos Yellow', U.S. Plant Pat. No. 29,974 |
|---|---|---|
| Plant size: | Similar | Similar |
| Plant habit: | Similar | Similar |

The male parent was an unnamed, unpatented proprietary seedling '14-M539'.

TABLE 2

Characteristics of the male parent, compared to 'CIFZ0110':

| Trait | 'CIFZ0110' | '14-M539' |
|---|---|---|
| Natural response: | ½ week faster | ½ week slower |
| Blackcloth response: | ¾ week faster | ¾ week slower |
| Flower size: | Similar | Similar |
| Flower color: | Yellow | Pink/White bicolor |
| Flower type: | Less disc florets | More disc florets |
| Plant size: | Bit smaller | Bit larger |
| Plant habit: | Similar | Similar |

The first act of asexual reproduction of 'CIFZ0110' was accomplished when vegetative cuttings were propagated from the initial selection in January 2021 in Alva, Florida.

BRIEF SUMMARY OF INVENTION

Horticultural examination of plants grown from cuttings of the plant initiated in January 2021 and continuing thereafter, has demonstrated that the combination of characteristics as herein disclosed for 'CIFZ0110' are firmly fixed and are retained through successive generations of asexual reproduction.

'CIFZ0110' has not been observed under all possible environmental conditions. The phenotype may vary significantly with variations in environment such as temperature, light intensity and day length.

A Plant Breeder's Right for this cultivar has not yet been applied for. 'CIFZ0110' has not been made publicly available prior to the effective filing date of this application, notwithstanding any disclosure that may have been made less than one year prior to the effective filing date of this application by the inventor or another who obtained 'CIFZ0110' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0110' with colors being as true as possible with an illustration of this type.

Figure 2:
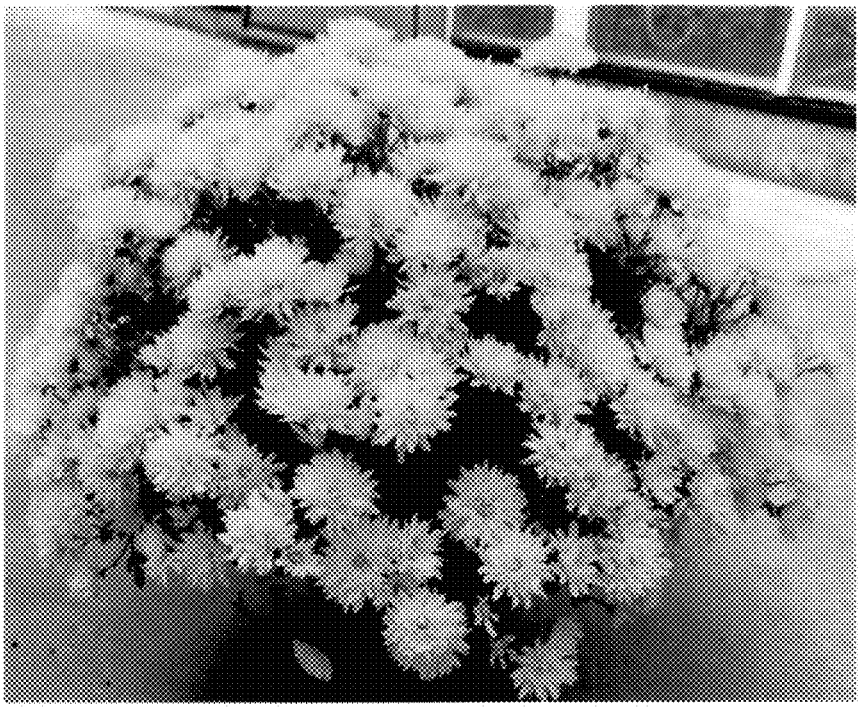

The photographic drawing shows in FIG. 1 a close view of flower of the new variety and in FIG. 2 a flowering plant from an indoor trial.

The aforementioned photographs: FIG. 1, as well as FIG. 2 were taken on Sep. 12, 2023 both showing a plant from the same blackcloth indoor trial in Enkhuizen, The Netherlands.

These plants were about 13 weeks of age. One rooted cutting per pot had been planted in a 15 cm pot, not pinched in week 23, 2023 and black clothed from week 29. Plants started flowering the end of August 2023.

The measurements were taken in Enkhuizen, The Netherlands, in September 2023 on plants from the same indoor blackcloth trial.

DIFFERENCES BETWEEN THE NEW VARIETY 'CIFZ0110' AND TWO MOST SIMILAR VARIETIES

TABLE 3

DIFFERENCES BETWEEN THE NEW VARIETY 'CIFZ0110' AND TWO MOST SIMILAR VARIETIES:

| Trait | 'CIFZ0110' | 'CIFZ0113', U.S. Plant Pat. No. 25,878 |
|---|---|---|
| Natural response: | Similar but faster in the heat | Similar but slower in the heat |
| Blackcloth response: | ½ week faster | ½ week slower |
| Flower color: | Similar | Similar |
| Flower type: | Similar | Similar |
| Plant size: | Bit larger | Bit smaller |
| Flowering uniformity: | More uniform | Less uniform |

TABLE 4

| Trait | 'CIFZ0110' | 'Sunrise Yellow', Not patented |
|---|---|---|
| Natural response: | Similar | Similar |
| Blackcloth response: | 1 week faster | 1 week slower |
| Flower size: | Similar | Similar |
| Flower color: | Bit darker yellow | Bit lighter yellow |

TABLE 4-continued

| Trait | 'CIFZ0110' | 'Sunrise Yellow', Not patented |
|---|---|---|
| Flower type: | Similar | Similar |
| Plant size: | Similar | Similar |
| Plant habit: | Similar | Similar |
| Foliage: | Darker green | Lighter green |
| Flowering uniformity: | Less uniform | More uniform |

DETAILED BOTANICAL DESCRIPTION

Color references are made to The Royal Horticultural Society Colour Chart (R.H.S.) 2001.

Plant:

*Form, growth and habit.*—Herbaceous garden-type, stems Upright and outwardly spreading, freely branching, strong and rather vigorous growth habit.

*Plant height* (*above soil*).—18 cm.

*Plant height* (*inflorescence included*).—21 cm.

*Plant width.*—40 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137B.

*Immature leaf, color lower surface.*—RHS 137C.

*Mature leaf, color, upper surface.*—RHS 137A.

*Mature leaf, color lower surface.*—RHS 137C.

*Length.*—6.0 cm.

*Width.*—3.0 cm.

*Shape.*—Ovate, with distinct lobes.

*Base shape.*—Attenuate.

*Apex shape.*—Acute.

*Margin.*—5 lobed.

*Number of margin indentations.*—15-19.

*Depth of margin indentations.*—2 mm.

*Leaf length terminal lobe relative to total leaf length.*—1:3.7.

*Leaf depth lower lateral sinus.*—1.4 cm.

*Texture, upper surface.*—Bifid hairs.

*Texture, lower surface.*—Bifid hairs.

*Color of veins, upper surface.*—RHS 139D.

*Color of veins, lower surface.*—RHS 139D.

*Pattern of veining.*—Palmate.

*Petiole color.*—RHS 139D.

*Petiole length.*—1.8 cm.

*Diameter.*—0.2 cm.

*Texture.*—Bifid hairs.

*Presence of stipules.*—No.

Stem:

*Quantity of main branches per plant.*—5.

*Color of stem.*—RHS 144C.

*Length of stem.*—11.0-14.0 cm.

*Diameter.*—0.3 cm.

*Length of internodes.*—1.0-1.5 cm.

*Texture.*—Bifid hairs.

*Color of peduncle.*—RHS 147C.

*Length of peduncle.*—2.5-3.0 cm.
*Peduncle diameter.*—0.2 cm.
*Texture.*—Bifid hairs.

Inflorescence:
*Type.*—Compositae, solitary, decorative inflorescences borne terminally above foliage, ligulate ray florets arranged in whorls on a capitulum giving a double flower.
*Quantity of short days to flowering (response time).*—Approximately 6 weeks.
*Quantity of inflorescences per plant.*—About 210 with some small buds developing.
*Lastingness of individual blooms on the plant.*—About six weeks from first color.
*Fragrance.*—Slightly spicy.

Bud (when showing color):
*Color.*—RHS 14B.
*Length.*—0.7 cm.
*Width.*—0.6 cm.
*Shape.*—Oblate.

Immature inflorescence (at moment of opening):
*Diameter.*—1.5-2 cm.
*Color of ray florets, upper surface.*—RHS 12A.
*Color of ray florets, lower surface.*—RHS 12B.

Mature inflorescence:
*Diameter.*—2.5-3.0 cm.
*Depth.*—2.0 cm.
*Total diameter of disc.*—Fully double flower so no disc present.
*Receptacle color.*—RHS 137A.
*Receptacle height.*—0.9 cm.
*Receptacle diameter.*—1.0 cm.
*Length of corolla tube.*—No tube.

Ray florets:
*Average quantity of florets.*—170.
*Color of florets, upper surface.*—RHS 9A.
*Color lower surface.*—RHS 8A.
*Length.*—1.1 cm.
*Width/diameter.*—0.3 cm.
*Average number of rows of ray florets.*—2.
*Shape.*—Oblong.
*Apex shape.*—Dentate.
*Base shape.*—Moderately concave.
*Margin.*—Entire. Small incisions may be present at tip.
*Margin.*—Type of rolling: Weakly involute.
*Texture, upper surface.*—Papillate.
*Lower surface.*—Papillate.
*Ribs present.*—Yes.
*Number of keels.*—1.
*Profile at widest point.*—Flat.
*Longitudinal axis shape.*—Weakly reflexing.
*Longitudinal axis curvature strength.*—Weak.
*Corolla tube shape.*—No tube.

Disc florets:
*Number of disc florets.*—0.

Inflorescence (at moment of senescence):
*Color of ray florets, upper surface.*—RHS 9B.
*Color of ray florets, lower surface.*—RHS 8A.

Phyllaries:
*Quantity.*—15.
*Color, upper surface.*—RHS 138B.
*Color, lower surface.*—RHS 138A.
*Length.*—0.5 cm.
*Width.*—0.1-0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.3 cm.
*Style color.*—RHS 157D.
*Style length.*—0.2 cm.
*Stigma color.*—RHS 5C.
*Stigma shape.*—Bi-parted.
*Ovary color.*—RHS 157C.
*Ovary length.*—0.2 cm.
*Ovary width.*—0.1 cm.

Androecium: None.
*Fertility/seed set.*—Has not been determined to date.
*Disease/pest resistance.*—Has not been determined to date.
*Hardiness.*—Has not been determined to date.

What is claimed is:

1. A new and distinct variety of *Chrysanthemum* plant named 'CIFZ0110' substantially as illustrated and described herein.

* * * * *